US010283337B2

(12) United States Patent
Takeda et al.

(10) Patent No.: US 10,283,337 B2
(45) Date of Patent: May 7, 2019

(54) MICROPARTICLE COMPOSITION ANALYZING APPARATUS

(71) Applicant: FUJI ELECTRIC CO., LTD., Kanagawa (JP)

(72) Inventors: Naoki Takeda, Yokohama (JP); Kazuhiro Koizumi, Sagamihara (JP); Takamasa Asano, Hino (JP); Yoshiki Hasegawa, Hino (JP)

(73) Assignee: FUJI ELECTRIC CO., LTD., Kanagawa (JP)

( * ) Notice: Subject to any disclaimer, the term of this patent is extended or adjusted under 35 U.S.C. 154(b) by 140 days.

(21) Appl. No.: 15/216,703

(22) Filed: Jul. 22, 2016

(65) Prior Publication Data

US 2017/0069476 A1 Mar. 9, 2017

(30) Foreign Application Priority Data

Sep. 9, 2015 (JP) ................................. 2015-177729

(51) Int. Cl.
*H01J 49/04* (2006.01)
*G01N 33/00* (2006.01)
*G01N 15/00* (2006.01)

(52) U.S. Cl.
CPC .......... *H01J 49/0463* (2013.01); *G01N 15/00* (2013.01); *G01N 33/0006* (2013.01); *G01N 33/0026* (2013.01); *G01N 33/0073* (2013.01); *G01N 33/0004* (2013.01); *G01N 33/007* (2013.01); *G01N 33/0016* (2013.01); *G01N 2015/0046* (2013.01); *G01N 2033/0019* (2013.01); *G01N 2033/0072* (2013.01); *H01J 49/0422* (2013.01)

(58) Field of Classification Search
CPC ......... G01N 33/007; G01N 2033/0072; G01N 33/0004; G01N 33/0006; G01N 33/0026; G01N 33/0016; G01N 2033/0019; G01N 33/0073; G01N 15/00; G01N 2015/0046; H01J 49/0422; H01J 49/0463
See application file for complete search history.

(56) References Cited

U.S. PATENT DOCUMENTS 4,063,446 A * 12/1977 Fuhrmann .............. G01N 27/12 261/107
4,316,382 A * 2/1982 Woodruff ............... G01N 27/18 73/23.2

(Continued)

FOREIGN PATENT DOCUMENTS

WO WO 00/42427 * 7/2000

*Primary Examiner* — Benjamin R Whatley

(57) ABSTRACT

Despite the desire to measure the composition and concentration of the microparticles included in a gaseous body sample serving as the measurement target, there is a problem that measurement cannot be performed accurately due to the effect of substances other than the gaseous body sample adsorbing to a trapping body of the analyzing apparatus that traps the microparticles, for example. Therefore, provided is a microparticle composition analyzing apparatus that analyzes composition of microparticles contained in a gaseous body sample, comprising a gas analyzer and a control section that sequentially introduces into the gas analyzer a comparative gas and a sample gas caused by the microparticles generated by irradiating the gaseous body sample with a laser.

15 Claims, 8 Drawing Sheets

(56) References Cited

U.S. PATENT DOCUMENTS

| | | | | |
|---|---|---|---|---|
| 6,040,574 | A | 3/2000 | Jayne et al. | |
| 6,432,721 | B1 * | 8/2002 | Zook | G01N 1/24 422/82 |
| 2001/0019844 | A1 * | 9/2001 | Kishkovich | G01N 33/0006 436/106 |
| 2003/0136176 | A1 * | 7/2003 | Ruiz | G01N 33/0016 73/23.2 |
| 2012/0096925 | A1 * | 4/2012 | Hansen | G01N 1/2205 73/28.04 |
| 2013/0011930 | A1 | 1/2013 | Takegawa et al. | |

* cited by examiner

MICROPARTICLE COMPOSITION ANALYZING APPARATUS

The contents of the following Japanese patent application are incorporated herein by reference:

NO. 2015-177729 filed on Sep. 9, 2015.

BACKGROUND

1. Technical Field

The present invention relates to a microparticle composition analyzing apparatus.

2. Related Art

Concern has been mounting about the health effects of particulate substances in the atmosphere (aerosol), and apparatuses are being developed that analyze the composition, concentration, and the like of these particulates.

PRIOR ART DOCUMENTS

Patent Documents

Patent Document 1: U.S. Pat. No. 6,040,574

Patent Document 2: International Publication 2011/114587

Despite the desire to measure the composition and concentration of the microparticles included in a gaseous body sample serving as the measurement target, there is a problem that measurement cannot be performed accurately due to the effect of substances other than the gaseous body sample adsorbing to a trapping body of the analyzing apparatus that traps the microparticles, for example. In particular, when the apparatus begins operating, the amount of impact this substance has changes according to each measurement timing due to changes in the measurement conditions, changes in the measurement environment, and the like.

SUMMARY

According to a first aspect of the present invention, provided is a microparticle composition analyzing apparatus that analyzes composition of microparticles contained in a gaseous body sample, comprising a gas analyzer and a control section that sequentially introduces into the gas analyzer a comparative gas and a sample gas caused by the microparticles generated by irradiating the gaseous body sample with a laser.

The microparticle composition analyzing apparatus may comprise a calculating section that calculates a difference amount between a specified component contained in a sample gas and the specified component contained in a comparative gas, as analyzed by the gas analyzer.

The comparative gas may be a gas generated by irradiating, with the laser, processed air that has undergone a cleaning process. At this time, the microparticle composition analyzing apparatus may further comprise an air generating section that generates the processed air that has undergone the cleaning process by filtering the gaseous body sample.

The control section may sequentially switch between the gaseous body sample and the processed air and supplies the corresponding gaseous body sample or processed air to a position irradiated by the laser. At this time, the control section may sequentially introduce into the gas analyzer the sample gas generated by pulse-irradiating the gaseous body sample with the laser and the comparative gas generated by pulse-irradiating the processed air with the laser. Instead, the control section may repeatedly introduce into the gas analyzer, in an alternating manner, the sample gas generated by continuously irradiating the gaseous body sample with the laser and the comparative gas generated by continuously irradiating the processed air with the laser.

If the sample gas and the comparative gas are repeatedly introduced into the gas analyzer in an alternating manner, the control section may introduce the sample gas and the comparative gas into the gas analyzer in an alternating manner with a predetermined period. Instead, the control section may introduce the sample gas and the comparative gas into the gas analyzer in an alternating manner with a timing adjusted based on output results of the gas analyzer. At this time, the control section may suspend radiation of the laser during a time period corresponding to a switch between the gaseous body sample and the processed air.

Instead of being a gas based on the processed air, the comparative gas may be a gas that is present near an irradiation position of the laser during a time period in which the gaseous body sample is not irradiated with the laser.

The control section may repeatedly introduce into the gas analyzer, in an alternating manner, the sample gas generated by irradiating the gaseous body sample with the laser and the comparative gas generated that is present near the irradiation position of the laser when the laser is not being radiated. At this time, the control section may introduce the sample gas and the comparative gas into the gas analyzer in an alternating manner with a predetermined period. Instead, the control section may introduce the sample gas and the comparative gas into the gas analyzer in an alternating manner with a timing adjusted based on output results of the gas analyzer.

The control section may determine whether to use gas generated by irradiating, with the laser, processed air obtained by performing a cleaning process on the comparative gas or gas that is present near an irradiation position of the laser during a time period in which the microparticles are not irradiated by the laser.

According to a second aspect of the present invention, the microparticle composition analyzing apparatus may comprise, in addition to all of the components of the microparticle composition analyzing apparatus of the first aspect, an acquiring section that acquires at least the gaseous body sample; a trapping section for trapping the microparticles released from the acquiring section; and a laser apparatus that radiates the laser toward the trapping section.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
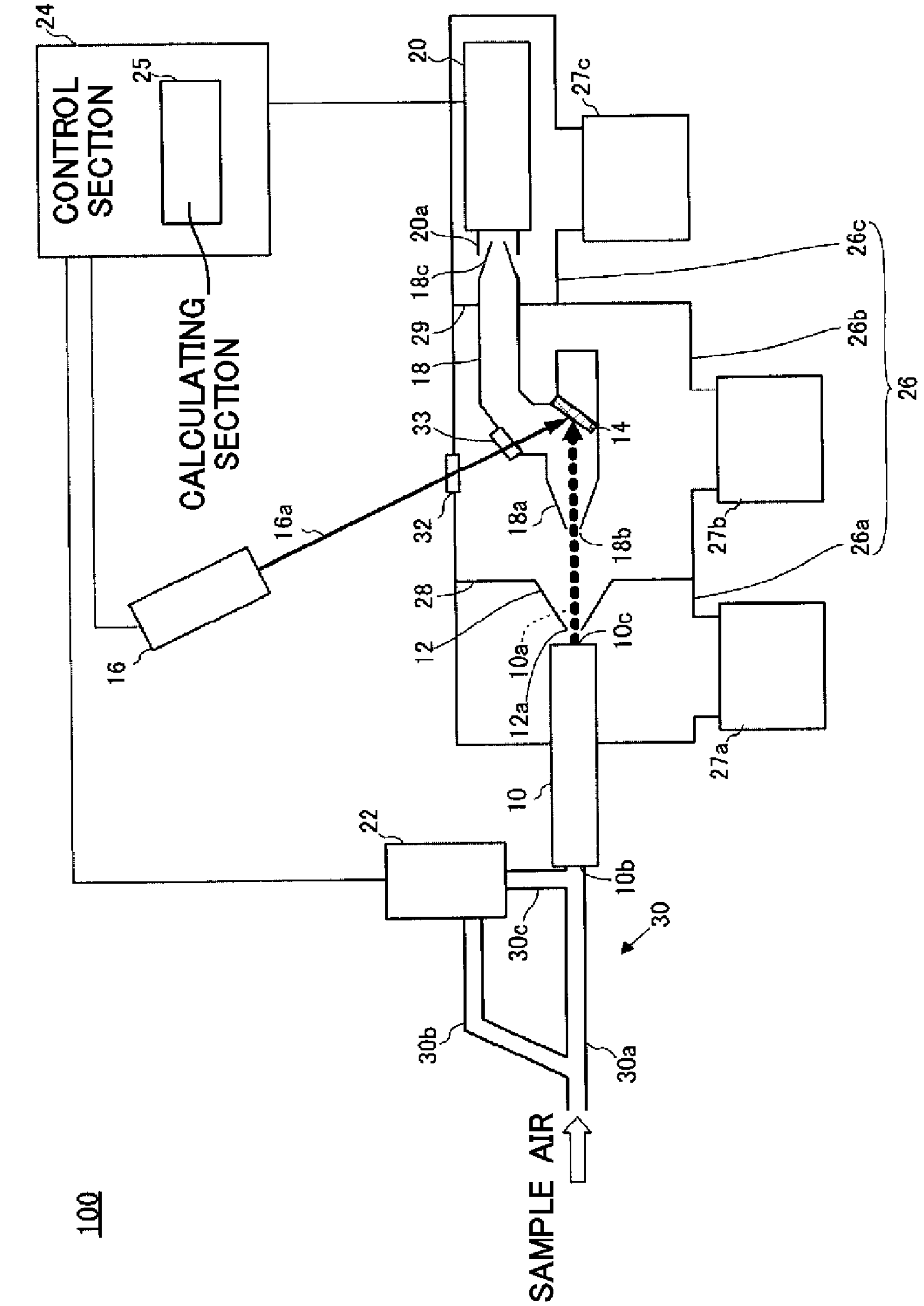
FIG. 1 is a schematic view for describing the structure of a microparticle composition analyzing apparatus according to a first embodiment.

FIG. 1 is a schematic view for describing the structure of a microparticle composition analyzing apparatus 100 according to a first embodiment. The microparticle composition analyzing apparatus 100 is an apparatus for analyzing the composition and concentration of microparticles included in a gaseous body sample (aerosol).

The microparticle composition analyzing apparatus 100 includes an aerodynamic lens 10, a skimmer 12, a trapping body 14, a laser apparatus 16, an analysis cell 18, a gas analyzer 20, and a processed air supplying section 22. Furthermore, the microparticle composition analyzing apparatus 100 includes a control section 24.

The microparticle composition analyzing apparatus 100 includes a reduced pressure chamber 26. The reduced pressure chamber 26 includes a first reduced pressure chamber 26*a*, a second reduced pressure chamber 26*b*, and a third reduced pressure chamber 26*c*. The first reduced pressure chamber 26*a* forms a first reduced pressure space therein. The second reduced pressure chamber 26*b* forms a second reduced pressure space therein. The third reduced pressure chamber 26*c* forms a third reduced pressure space therein. The first reduced pressure chamber 26*a* and the second reduced pressure chamber 26*b* are partitioned from each other by a first dividing wall 28. The second reduced pressure chamber 26*b* and the third reduced pressure chamber 26*c* are partitioned from each other by a second dividing wall 29. Accordingly, the overall reduced pressure chamber 26 is separated into three compartments.

The first reduced pressure chamber 26*a* includes a first exhaust apparatus 27*a*. The second reduced pressure chamber 26*b* includes a second exhaust apparatus 27*b*. The third reduced pressure chamber 26*c* includes a third exhaust apparatus 27*c*. The first exhaust apparatus 27*a*, the second exhaust apparatus 27*b*, and the third exhaust apparatus 27*c* reduce the pressures in the first reduced pressure space, the second reduced pressure space, and the third reduced pressure space to have predetermined internal pressures that are different from each other. The predetermined internal pressures in the first reduced pressure space, the second reduced pressure space, and the third reduced pressure space may respectively be $10^{-3}$ Torr $10^{-5}$ Torr, and $10^{-7}$ Torr, for example.

The aerodynamic lens 10 is arranged in a manner to be inserted through the first reduced pressure space from one side surface of the first reduced pressure chamber 26*a*. Specifically, the aerodynamic lens 10 is arranged such that an inlet side into which the gaseous body sample or the like is introduced is positioned outside of the first reduced pressure chamber 26*a* and an emission opening 10*c* side for emitting a particle stream 10*a* is arranged inside of the first reduced pressure chamber 26*a*. The aerodynamic lens 10 is connected to an inlet pipe 30 that selectively guides the sample air, which is the gaseous body sample, and processed air, which is described further below. The aerodynamic lens 10 gathers the microparticles contained in the gas introduced from the inlet pipe 30, and emits these microparticles as the particle stream 10*a*. In the microparticle composition analyzing apparatus 100, the aerodynamic lens 10 serves as an acquiring section that acquires the sample air. The details of the aerodynamic lens 10 are described below using the drawings.

The skimmer 12 is provided to the first dividing wall 28 that partitions the first reduced pressure chamber 26*a* and the second reduced pressure chamber 26*b* from each other. The skimmer 12 is a structure shaped as a cone in which a through-hole 12*a* is formed in the vertex, and is arranged such that the through-hole 12*a* faces the emission opening 10*c* of the aerodynamic lens 10. As described above, since the internal pressure of the second reduced pressure space is set to be lower than the internal pressure of the first reduced pressure space, gas flow occurs from the first reduced pressure space to the second reduced pressure space via the through-hole 12*a*. When the particle stream 10*a* emitted from the aerodynamic lens 10 passes through the through-hole 12*a*, the skimmer 12 removes a portion of surplus gas contained in the particle stream 10*a*.

A front end of the analysis cell 18 is arranged within the second reduced pressure chamber 26*b*, and a back end of the analysis cell 18 is provided in a manner to be inserted through the second dividing wall 29 partitioning the second reduced pressure chamber 26*b* and the third reduced pressure chamber 26*c* from each other. The front end of the analysis cell 18 is provided with a skimmer portion 18*a*. The skimmer portion 18*a* is shaped as a cone with a through-hole 18*b* provided at the vertex, in the same manner as the skimmer 12. The through-hole 18*b* is arranged on a straight line joining the emission opening 10*c* of the aerodynamic lens 10 to the through-hole 12*a* of the skimmer 12. The skimmer portion 18*a* further removes surplus gas contained in the particle stream 10*a*.

The back end of the analysis cell 18 also forms a tapered shape, and this end has a microhole 18*c*. In this way, by forming both ends of the analysis cell 18 as tapered shapes, the microparticle composition analyzing apparatus 100 can maintain the pressure difference between the second reduced pressure space of the second reduced pressure chamber 26*b* and the third reduced pressure space of the third reduced pressure chamber 26*c*. Accordingly, a gas flow is created within the analysis cell 18 from the second reduced pressure chamber 26*b* toward the third reduced pressure chamber 26*c*. Furthermore, the trapping body 14 is arranged near the central portion of the analysis cell 18, such that the analysis cell 18 has an overall crank shape causing the gas generated by the trapping body 14 to be gathered and moved toward the microhole 18*c*.

The trapping body 14 is provided behind the skimmer portion 18*a* within the analysis cell 18. The trapping body 14 is arranged such that the surface for trapping the microparticles is oblique to the flow direction of the particle stream 10*a*. The trapping body 14 functions as a trapping section for trapping the microparticles emitted from the aerodynamic lens 10. The trapping body 14 has a mesh structure, and traps the microparticles contained in the particle stream 10*a* incident thereto.

Each microparticle contained in the particle stream 10*a* incident to the trapping body 14 collides with the mesh structure with a unique probability. A microparticle that has collided with the mesh structure then repeatedly collides with the mesh structure many times and slows down with each collision. This microparticle gradually loses speed until finally being trapped by the trapping body 14.

The laser apparatus 16 is arranged outside of the reduced pressure chamber 26. The laser apparatus 16 oscillates a laser 16*a*. An optical window 32 is provided on a side wall of the second reduced pressure chamber 26*b* in contact with the outside atmosphere. Furthermore, an optical window 33 is provided on a side wall of the analysis cell 18. The laser apparatus 16 radiates the laser 16*a* to the trapping body 14 through the optical window 32 and the optical window 33, and heats the radiated portions. In this embodiment, a carbon dioxide gas ($CO_2$) laser is used as an example of the laser 16*a*.

The laser apparatus 16 vaporizes, sublimates, or causes a reaction with the microparticles trapped by the trapping body 14 using the laser 16*a*, thereby generating gas that is a desorbed component. Here, the term "desorbed component" refers to a component that is desorbed from the state of being trapped by the trapping body 14 and enters a mobile state. In the following description, the gas that is a desorbed component when the sample air is introduced may be referred to as the "sample gas." Specifically, the sample gas component is $CO_2$, $H_2O$, $NO_2$, $SO_2$, and the like generated by the oxidization of the structural components of the microparticles.

The gas analyzer 20 is arranged within the third reduced pressure chamber 26*c*. The gas analyzer 20 is an analyzer that analyzes the components of gas introduced thereto using mass spectrometry. Mass spectrometry has a relatively low minimum detection threshold, and therefore can be suitably used for sample air having a relatively low microparticle concentration. An analyzer that uses mass spectrometry to analyze the gas components is used in the present embodiment, but an analyzer that analyzes the gas component using another analysis method can be adopted according to the concentration, type, and the like of the microparticles in the gaseous body sample serving as the analysis target. For example, when there is a high concentration of microparticles that are analysis targets, an analyzer that utilizes spectral analysis may be adopted.

The gas analyzer 20 includes an ionization region 20*a*. The gas analyzer 20 is arranged such that the ionization region 20*a* is opposite the microhole 18*c* in the tapered shape formed on the back end of the analysis cell 18. The ionization region 20*a* ionizes the gas introduced from the analysis cell 18, and supplies this ionized gas to the gas analyzer 20. The gas analyzer 20 periodically outputs to a calculating section 25, which is described further below, an intensity signal corresponding to the content of each component in the introduced gas.

The inlet pipe 30 branches midway through into a first path 30*a* and a second path 30*b*, and the first path 30*a* is directly connected to the inlet 10*b* of the aerodynamic lens 10. The second path 30*b* is connected to the processed air supplying section 22. The processed air supplying section 22 sucks in the sample air from the second path 30*b*. The processed air supplying section 22 includes a filter formed by a HEPA filter, an electrical dust collector, and the like, and performs a cleaning process to remove microparticles from the sample gas. In the following description, the sample air that has undergone the cleaning process using the processed air supplying section 22 may be referred to as "processed air." The processed air supplying section 22 expels the processed air to the third path 30*c* of the inlet pipe 30. In this series of processes, the processed air supplying section 22 functions as an air generating section that generates processed air. The third path 30*c* is connected to the first path 30*a* near the inlet 10*b* of the aerodynamic lens 10.

In the branching inlet pipe 30, the first path 30*a* is connected in a straight line to the inlet 10*b* of the aerodynamic lens 10. In other words, the acquired sample air reaches the inlet 10*b* of the aerodynamic lens 10 without having its flow impeded. On the other hand the second path 30*b* branches in a direction forming an acute angle relative to the downstream portion of the first path 30*a*. However, when performing the cleaning process, the processed air supplying section 22 sucks in the sample air from the second path 30*b*, and therefore it is possible to acquire the necessary amount of the sample air.

The control section 24 performs overall control of the operation and processing of each configurational component of the microparticle composition analyzing apparatus 100. Furthermore, the control section 24 includes a calculating section 25 that calculates the output of the gas analyzer 20. Specifically, the calculating section 25 uses the intensity signal corresponding to the content of a specified component acquired from the gas analyzer 20 by the control section 24 to perform various calculations. As one example of this, the calculating section 25 calculates the difference amount between the specified component included in the sample gas and in a comparative gas, as analyzed by the gas analyzer 20. In the present embodiment, a "comparative gas" is a gas generated by radiating laser into the processed air that has been cleaned by the processed air supplying section 22.

The control section 24 performs control such that the comparative gas and the sample gas caused by the microparticles contained in the sample air generated by irradiating the sample air with laser are introduced sequentially into the gas analyzer. Specifically, by controlling the processed air supplying section 22, the control section 24 sequentially switches between the sample air and the processed air as the air being supplied to the trapping body 14, which is at the position irradiated by the laser 16*a*. Then, by irradiating the trapping body 14 with the laser 16*a*, the sample gas is generated when the sample air is supplied and the comparative gas is generated when the processed air is supplied, and these gases are repeatedly introduced to the gas analyzer 20 in an alternating manner. At this time, the control section 24 causes the laser apparatus 16 to continuously radiate the laser 16*a*.

The following describes the method by which the control section 24 switches between the sample air and the processed air. By sucking in the sample air from the second path 30*b*, the processed air supplying section 22 can expel the processed air to the third path 30*c* with a greater flow rate than the critical flow rate determined by the diameter of the inlet 10*b* of the aerodynamic lens 10. The critical flow rate is approximately 100 CCM when the diameter of the inlet 10*b* is 0.1 mm. When controlling the processed air supplying section 22 to expel the processed air with a flow rate greater than or equal to this critical flow rate, the control section 24 can supply the aerodynamic lens 10 with only the processed air, without allowing the sample air that has not undergone the cleaning process to reach the inlet 10*b*.

The method for switching between the sample air and the processed air is not limited to a method of increasing and decreasing the flow rate of the processed air. For example, a three-way valve may be arranged at the point of intersection between the flow path of the sample air and the flow path of the processed air, and the control section 24 may be configured to perform switching control. The three-way valve used in this manner preferably has a structure that does not cause microparticles within the sample air to adsorb to the inside of the valve. A solenoid valve, ball valve, or the like can be adopted as the three-way valve.

When gas generated from an amount of microparticles that is greater than a minimum amount is introduced, the gas analyzer 20 can perform an analysis of these microparticles. The number of microparticles trapped by the trapping body 14 per unit time is proportional to the number of microparticles flowing to the trapping body 14 per unit time. Accordingly, the number of microparticles trapped by the trapping body 14 over a constant time changes according to the flow speed of the particle stream 10*a* and the density of microparticles contained in the particle stream 10*a*. In a case where the flow speed of the particle stream 10*a* is constant, the number of microparticles trapped by the trapping body 14 per unit time is greater when the concentration of microparticles contained in the sample air serving as the analysis target is higher.

In a case where the flow speed of the particle stream 10*a* is constant, the time needed for the minimum amount of microparticles necessary for enabling analysis to be trapped by the trapping body 14 is substantially inversely proportional to the concentration of microparticles included in the sample air. Accordingly, an amount of microparticles greater than the minimum amount needed for analysis is captured in a shorter time when the concentration of microparticles contained in the introduced sample air is higher. In other words, the gas analyzer 20 can perform the analysis processes in shorter cycles when the concentration of microparticles contained in the introduced sample air is higher.

Figure 2:
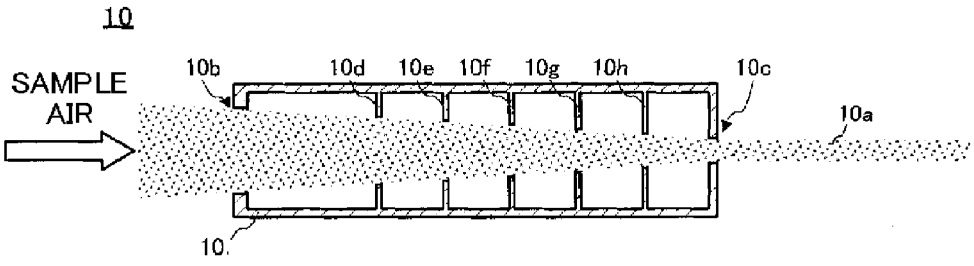
FIG. 2 is a schematic view for describing the aerodynamic lens.

FIG. 2 is a schematic view for describing the aerodynamic lens 10. The aerodynamic lens 10 includes a case 10*i* that has a cylindrical outer structure. The inlet 10*b* through which the sample air and the like are introduced from the outside is provided on the side surface at one end of the case 10*i*. Furthermore, the emission opening 10*c* that emits the particle stream 10*a* is provided on the side surface at the other end of the case 10*i*. The aerodynamic lens 10 includes orifices 10*d*, 10*e*, 10*f*, 10*g*, and 10*h* within the case 10*i*. The orifices 10*d* to 10*h* are donut-shaped plates having through-holes in their centers. As shown in FIG. 2, the diameters of the through-holes in the orifices 10*d* to 10*h* are formed to become respectively smaller in the stated order.

As described using FIG. 1, the inlet 10*b* and the emission opening 10*c* are respectively arranged outside and inside the first reduced pressure chamber 26*a*. Therefore, according to the pressure difference between the inlet 10*b* and the emission opening 10*c*, the sample air flows from the inlet 10*b* toward emission opening 10*c*. When passing out of the aerodynamic lens 10, the air that is the medium of the sample air moves while scattering. Therefore, the movement of the air, which is a gas, is impeded by each of the orifices.

On the other hand, the microparticles formed by solids or liquids tend to move in a straight line. Therefore, after passing through the first-stage orifice 10*d*, the microparticles are not significantly impeded as a result of moving through the second-stage and following orifices 10*e* to 10*h*. Furthermore, as described above, the diameters of the through-holes become gradually smaller from the orifice 10*d* to the orifice 10*h*, and therefore the flow path gradually constricts from the inlet 10*b* toward the emission opening 10*c*. Accordingly, the microparticles contained in the sample air introduced from the inlet 10*b* are arranged in a beam and emitted from the emission opening 10*c*.

Figure 3:
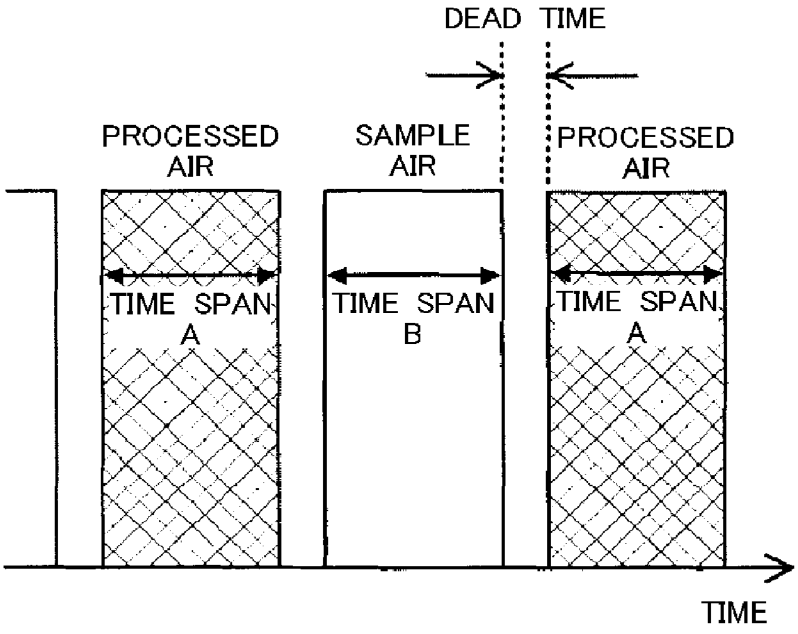
FIG. 3 is a drawing for describing the switching of the introduced gas.

FIG. 3 is a drawing for describing the switching of the introduced gas by the control section 24. In FIG. 3, the horizontal axis indicates time. The vertical axis indicates the target air introduction amount at each time. The portions with hash marks represent the processed air, and the empty white portions represent the sample air. As shown in the drawing, the profile of the introduced gas shown as target values switches in an alternating manner between the processed air and the sample air as pulses. Here, there is a dead time seen as a blank time provided during the time span of the switching between the processed air and the sample air. The surface area of each hash-marked portion represents the target introduction amount of the processed air, and the surface area of each empty white portion represents the target introduction amount of the sample air.

In the example of FIG. 3, the control section 24 performs control such that the processed air and the sample air are introduced into the aerodynamic lens 10 in an alternating manner with a predetermined period. In the example shown in the drawing, the time resulting from the combination of a time span A, a time span B, and two dead times is one period. The processed air and sample air introduced in this way are changed into gases near the surface of the trapping body 14 and introduced into the gas analyzer 20 in an alternating manner as the comparative gas and sample gas. Furthermore, the control section 24 does not acquire an output signal from the gas analyzer 20 during time spans corresponding to the dead times. At this time, the control section 24 may halt the radiation of the laser 16*a* during the time spans corresponding to the dead times.

Figure 4:
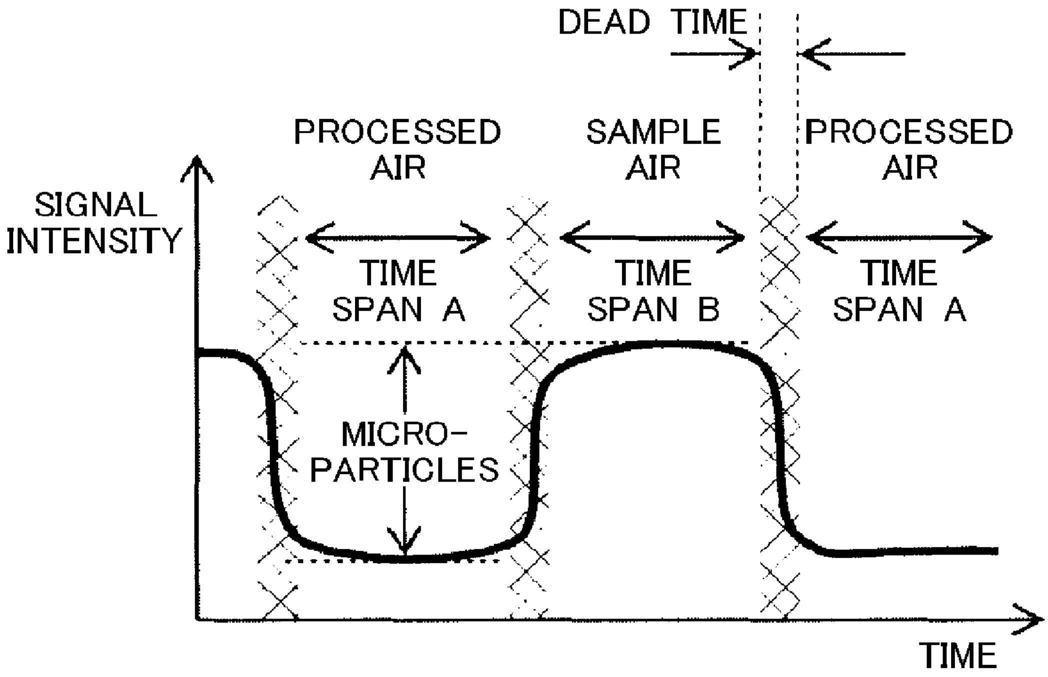
FIG. 4 shows an exemplary change of output from the gas analyzer corresponding to the introduced gas profile shown in FIG. 3.

FIG. 4 shows an exemplary change of output from the gas analyzer 20 corresponding to the introduced gas profile shown in FIG. 3. More specifically, the change over time is shown for the signal intensity of a specified component that is the observation target among the components of the gas introduced to the gas analyzer 20. In FIG. 4, the vertical axis indicates the signal intensity and the horizontal axis indicates time.

In FIG. 4, the hash-marked portions indicate dead times. Each time span A indicates change over time of the signal intensity in the time spans during which the processed air is being introduced. The time span B indicates change over time of the signal intensity in the time span during which the sample air is being introduced.

As described using FIG. 1, the processed air results from the microparticles being removed from the sample air by the cleaning process performed by the processed air supplying section 22. Therefore, during the time span A, the signal intensity output from the gas analyzer 20 should be zero. However, there are cases where segment components of finite intensity appear as noise components due to the effect of materials other than the gaseous body sample adsorbing to the trapping body 14 that traps the microparticles, for example. In FIG. 4, these segment components are shown in the time span A. Furthermore, the segment components are also included in the signal intensity during the time span B. Accordingly, the difference amount between the signal intensity during the time span B in which the sample air is introduced and the signal intensity during the time span A in which the processed air is introduced is the signal intensity caused by the specified component of the microparticles contained in the sample air. By setting this signal intensity difference amount as a fixed quantity in the calculating section 25, it is possible to measure the concentration of microparticles contained in the introduced sample air.

Figure 5:
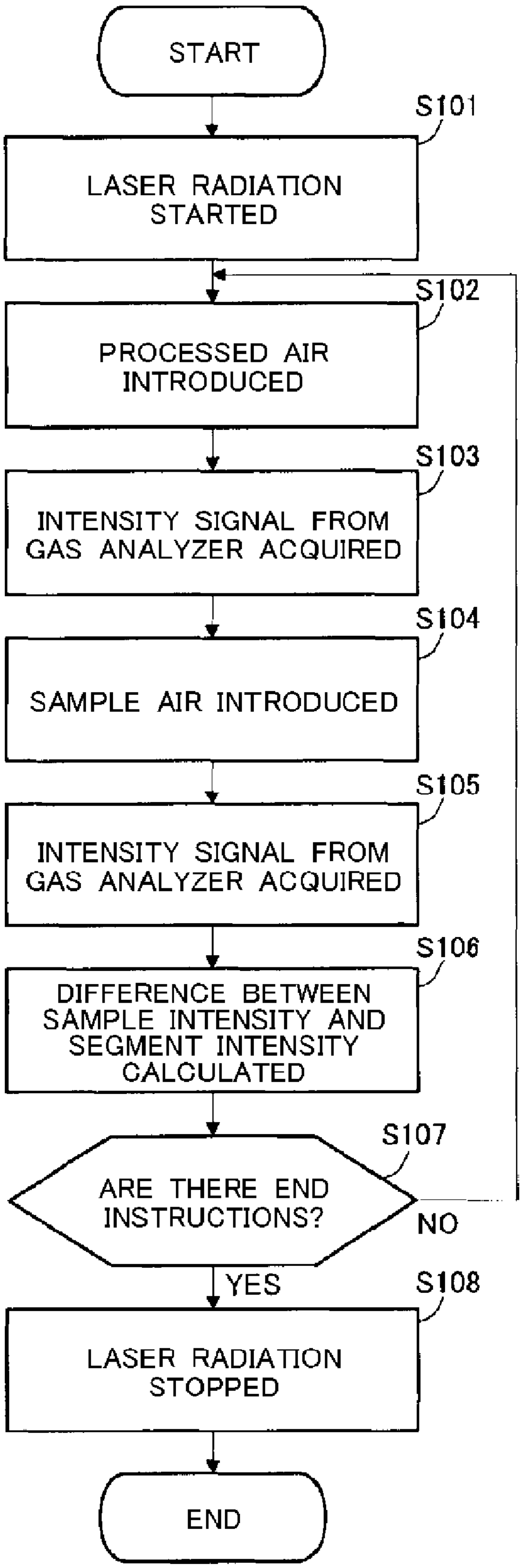
FIG. 5 is a flow chart describing an exemplary operation of the microparticle composition analyzing apparatus.

FIG. 5 is a flow chart describing an exemplary operation of the microparticle composition analyzing apparatus 100. This flow is started when the microparticle composition analyzing apparatus 100 receives instructions to begin analyzing the sample air from a user.

The control section 24 causes the laser apparatus 16 to begin radiating the laser 16*a* (step S101). Next, the control section 24 introduces the processed air into the aerodynamic lens 10 according to the introduced air profile (step S102).

Next, the control section 24 acquires the intensity signal of the specified component in the comparative gas from the gas analyzer 20 (S103). Specifically, the control section 24 acquires the intensity value at the sampling period of the gas analyzer 20, and judges that the output is stable when the change between intensity values at consecutive points is within a predetermined fluctuation range. The intensity value at this timing is determined to be a representative intensity value for the comparative gas in this time span. Of course, the intensity values at several points from a stable point may be averaged and this average value may be determined to be the representative intensity value. In the following description, the representative value corresponding to the comparative gas may be referred to as the "segment intensity."

Next, the control section 24 introduces the sample air into the aerodynamic lens 10 according to the introduced gaseous body profile (step S104). Specifically, the control section 24 stops the supply of processed air from the processed air supplying section 22.

Next, the control section 24 acquires the intensity signal of the specified component in the sample gas from the gas analyzer 20 (step S105). Specifically, in the same manner as the process performed for the processed air, the control section 24 acquires the intensity value at the sampling period of the gas analyzer 20, and judges that the output is stable when the change between intensity values at consecutive points is within a predetermined fluctuation range. The intensity value at this timing is determined to be a representative intensity value for the sample gas in this time span. Of course, the intensity values at several points from a stable point may be averaged and this average value may be determined to be the representative intensity value. In the following description, the representative value corresponding to the sample gas may be referred to as the "sample intensity."

Next, the calculating section 25 of the control section 24 calculates the difference amount between the sample intensity and the segment intensity (step S106). Specifically, the calculating section 25 determines the difference amount by subtracting the segment intensity from the sample intensity. The calculating section 25 calculates the concentration of microparticles in the observation target from the determined difference amount, the sampling period of the gas analyzer 20, the amount of the sample air introduced per unit time, and the like. The control section 24 displays the calculation results in a display section to be seen by the user and/or stores the calculation results in a storage section to maintain a record. Of course, the calculation results may be transmitted to an external device via an interface.

Next, the control section 24 judges whether there are end instructions from the user (step S107). If it is determined that there are no end instructions from the user, the control section 24 returns to step S102 and continues the measurement control. On the other hand, if it is judged that there are end instructions from the user, the control section 24 stops the laser apparatus 16 from radiating the laser 16*a* (step S108) and this process flow is ended.

As described above, in the present embodiment, the control section 24 controls the switching between the sample air and the processed air such that the sample gas and the comparative gas are introduced into the gas analyzer in an alternating manner with a predetermined period. However, instead of using a constant period, the control section 24 may adjust the timing for switching between the sample gas and the comparative gas by performing feedback control. Specifically, as soon as the output of the gas analyzer 20 is stable and the sample intensity and segment intensity are determined, the control section 24 switches the target being introduced into the aerodynamic lens 10 from the sample air to the processed air or from the processed air to the sample air. If this type of feedback control is performed, it is possible to increase the number of analyses performed per unit time.

Figure 6:
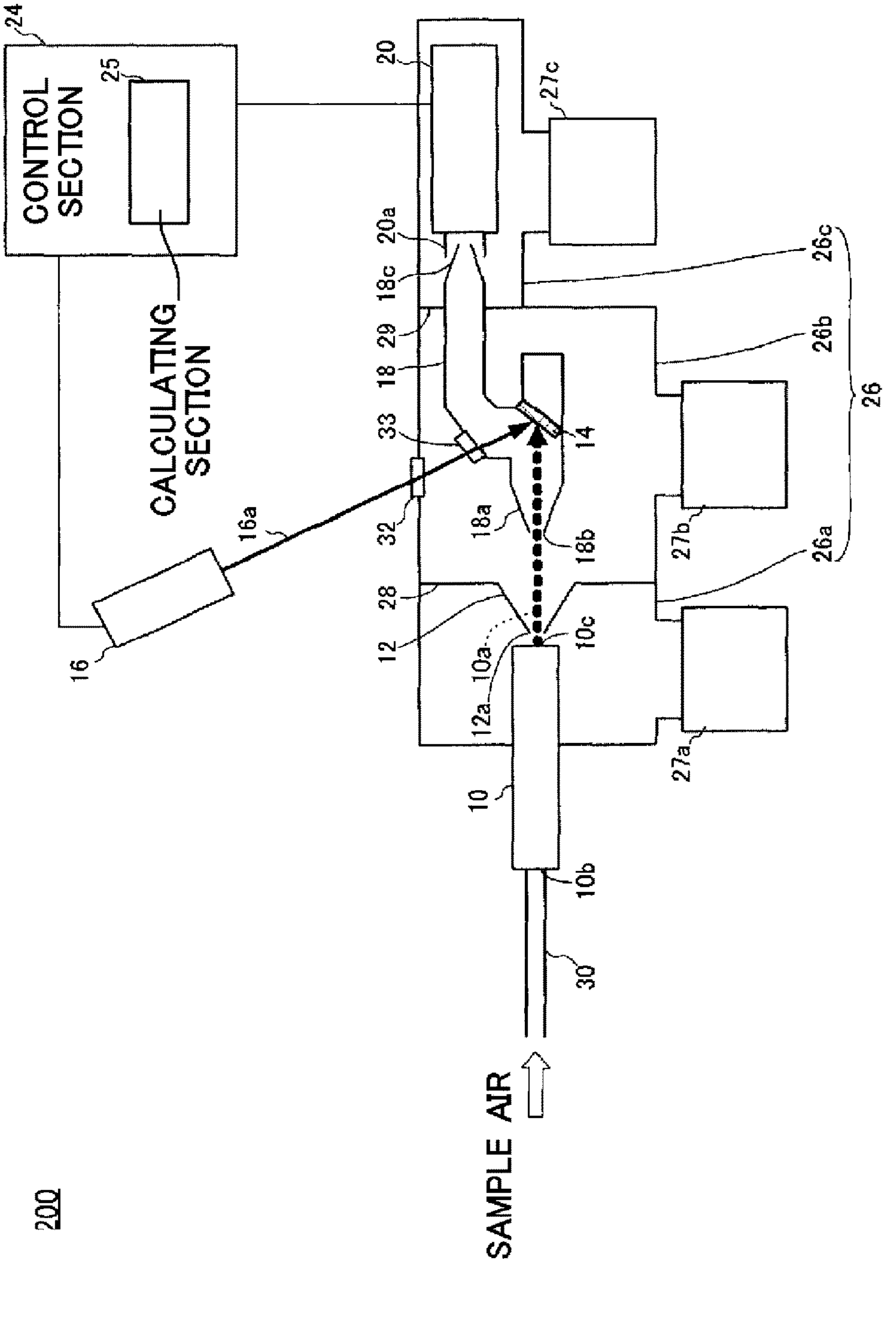
FIG. 6 is a schematic view for describing the structure of a microparticle composition analyzing apparatus according to a second embodiment.

FIG. 6 is a schematic view for describing the structure of a microparticle composition analyzing apparatus 200 according to a second embodiment. Aside from the processed air supplying section 22 of the microparticle composition analyzing apparatus 100 of the first embodiment being removed, the microparticle composition analyzing apparatus 200 has the same structure as the microparticle composition analyzing apparatus 100. Since the microparticle composition analyzing apparatus 200 does not include the processed air supplying section 22, the inlet pipe 30 is connected to the inlet 10*b* of the aerodynamic lens 10 as a single straight path. In the following description, shared components are given the same reference numerals and redundant descriptions are omitted.

In the present embodiment, the control section 24 controls the timing of the oscillation of the laser 16*a* of the laser apparatus 16. In other words, the control section 24 controls the timing of the starting and ending of the radiation of the laser 16*a*. The microparticle composition analyzing apparatus 200 according to the present embodiment sets the comparative gas to be the gas present near the trapping body 14, which is at the position being irradiated by the laser 16*a*, during the time period when the sample air is not being irradiated by the laser 16*a*, and analyzes the microparticles contained in the sample air. The microparticle composition analyzing apparatus 200 is suitable for the microparticle analysis of refractory compounds, e.g. ammonium sulfide, for which the vaporization of microparticles trapped by the trapping body 14 stops when the oscillation output of the laser apparatus 16 is weakened.

Figure 7:
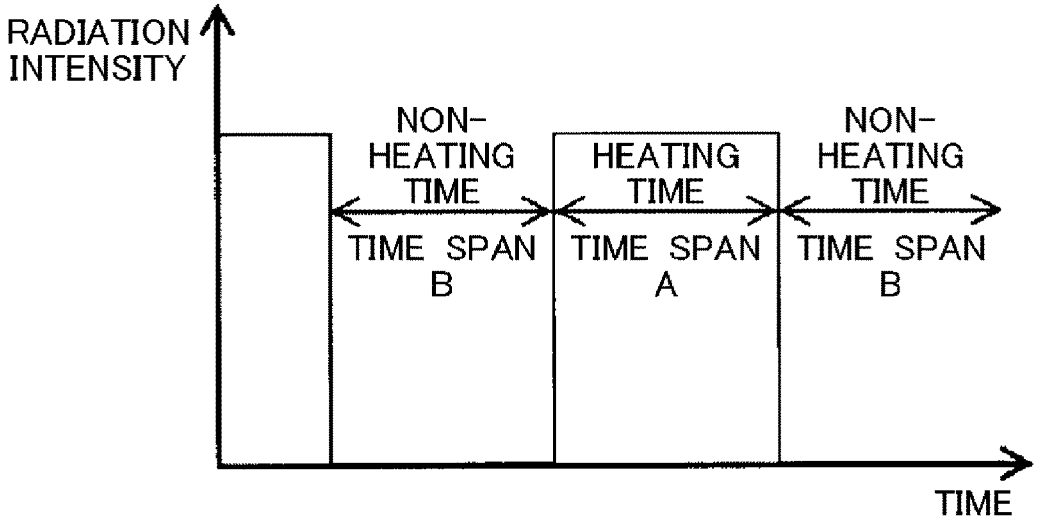
FIG. 7 is a drawing for describing the radiation timing of the laser.

FIG. 7 is a drawing for describing the radiation timing of the laser 16*a* by the control section 24. In FIG. 7, the horizontal axis indicates time and the vertical axis indicates the target radiation intensity of the laser 16*a* at each time. As shown in the drawing, the radiation profile indicating the target values switches between radiation intensities of the laser 16*a* in an alternating manner as pulses. The time span in which the laser 16*a* has radiation intensity represents the time when the sample air is being heated, and the time spans in which the radiation intensity is zero represent the time when the sample gas is not being heated. In the example of the drawing, the time resulting from the combination of a time span A that is a heating time and a time span B that is a non-heating time is one period. By controlling the timing at which the radiation of the laser 16*a* starts and ends in this way, the control section 24 causes the comparative gas and the sample gas to be introduced into the gas analyzer 20 in an alternating manner.

Figure 8:
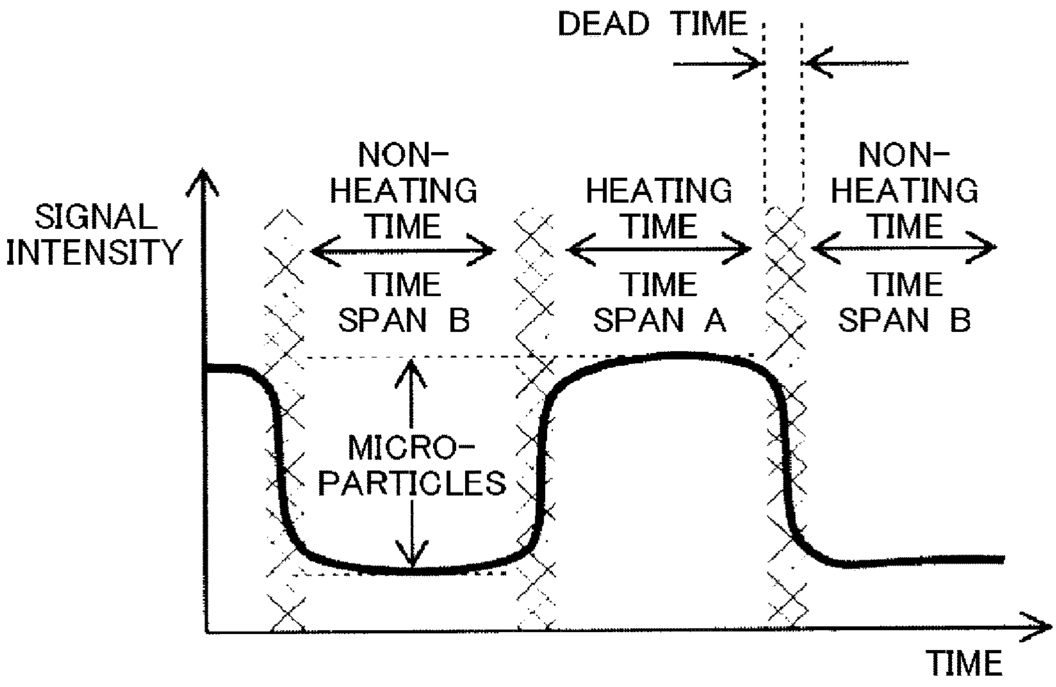
FIG. 8 shows an exemplary change in output from the gas analyzer corresponding to the radiation profile shown in FIG. 7.

FIG. 8 shows an exemplary change in output from the gas analyzer 20 corresponding to the radiation profile shown in FIG. 7. More specifically, in the same manner as FIG. 4, the change over time is shown for the signal intensity of a specified component that is the observation target among the components of the gas introduced to the gas analyzer 20. In FIG. 8, the vertical axis indicates the signal intensity and the horizontal axis indicates time. Descriptions of content that is identical to the content described using FIG. 4 are omitted.

The time span A indicates the change over time of the signal intensity in the time span during which the laser 16*a* is radiated. The time spans B indicate the change over time of the signal intensity in the time spans during which the laser 16*a* is not radiated.

If the microparticles of the analysis target are refractory, the signal intensity output from the gas analyzer 20 during a time span B should be zero. However, there are cases where finite intensity segment components appear as noise due to the effect of noise components that change over time, for example. In FIG. 8, these segment components are shown in the time spans B. Furthermore, the segment components are also included in the signal intensity in the time span A. Accordingly, the difference amount between the signal intensity in a time span A during which the laser 16*a* is radiated and the signal intensity in a time span B during which the laser 16*a* is not radiated is the signal intensity caused by the specified component of the microparticles contained in the sample air. By setting this signal intensity difference amount as a fixed quantity in the calculating section 25, it is possible to measure the concentration of microparticles contained in the introduced sample air.

Figure 9:
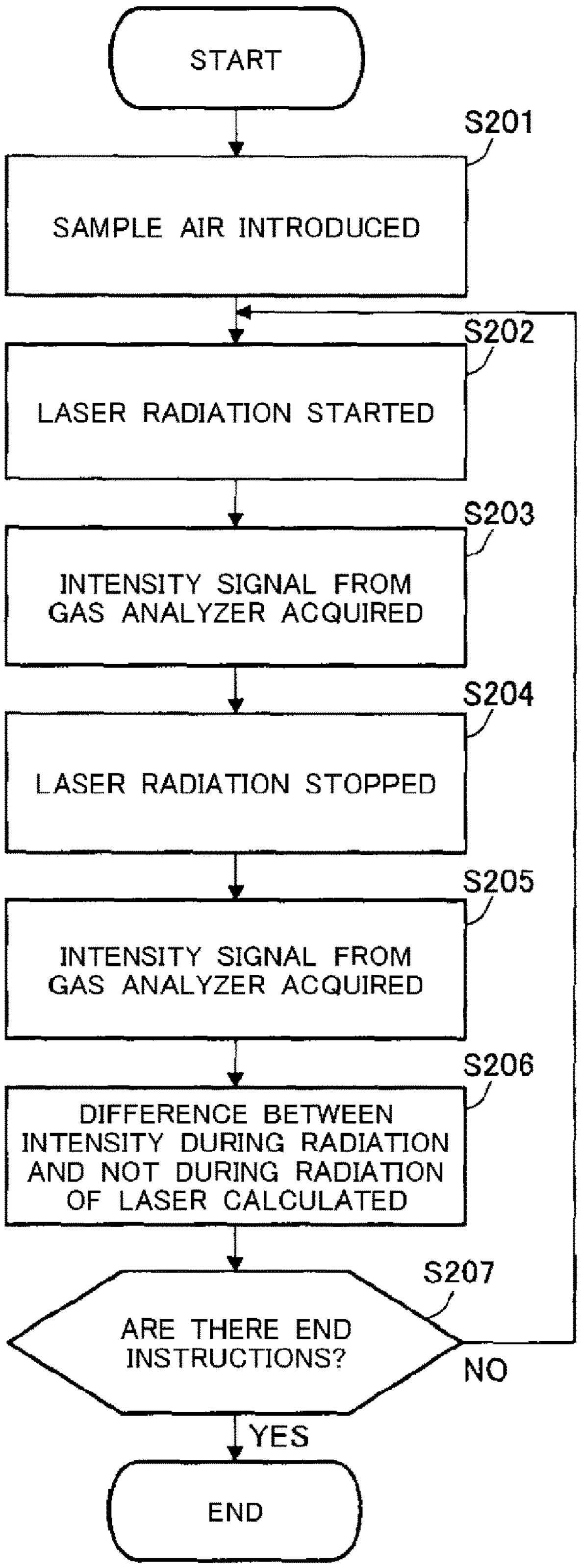
FIG. 9 is a flow chart describing an exemplary operation of the microparticle composition analyzing apparatus.

FIG. 9 is a flow chart describing an exemplary operation of the microparticle composition analyzing apparatus 200. FIGS. 7 and 8 show an example of control performed by the control section 24 in which the laser 16*a* is radiated with a predetermined period. FIG. 9 describes another example of control performed by the control section 24 in which the laser 16*a* is radiated at a timing adjusted based on the output results from the gas analyzer 20. In the same manner as the flow described using FIG. 5, this flow is started when the microparticle composition analyzing apparatus 200 receives instructions to begin analyzing the sample air from the user.

The control section 24 introduces the sample air (step S201). For example, the control section 24 introduces the sample air into the aerodynamic lens 10 in a manner to maintain a certain flow rate per unit time by controlling a valve provided to the inlet pipe 30. Next, the control section 24 causes the laser apparatus 16 to begin radiating the laser 16*a* (step S202).

Next, the control section 24 acquires the intensity signal of the specified component in the sample gas from the gas analyzer 20 (S203). Specifically, the control section 24 acquires the intensity value at the sampling period of the gas analyzer 20, and judges that the output is stable when the change between intensity values at consecutive points is within a predetermined fluctuation range. The intensity value at this timing is determined to be the sample intensity, which is the representative intensity value for the sample gas in this time span. Of course, the intensity values at several points from a stable point may be averaged and this average value may be determined to be the sample intensity value.

When the sample intensity has been determined, the control section 24 stops the radiation of the laser 16*a* (step S204). Next, the control section 24 acquires the intensity signal of the specified component in the comparative gas from the gas analyzer 20 (S205). Specifically, the control section 24 acquires the intensity value at the sampling period of the gas analyzer 20, and judges that the output is stable when the change between intensity values at consecutive points is within a predetermined fluctuation range. The intensity value at this timing is determined to be the segment intensity, which is the representative intensity value for the comparative gas in this time span. Of course, the intensity values at several points from a stable point may be averaged and this average value may be determined to be the representative intensity value.

Next, the calculating section 25 of the control section 24 calculates the difference amount between the sample intensity and the segment intensity (step S206). Specifically, the calculating section 25 determines the difference amount by subtracting the segment intensity from the sample intensity. The calculating section 25 calculates the concentration of microparticles in the observation target from the determined difference amount, the sampling period of the gas analyzer 20, the amount of the sample air introduced per unit time, and the like. The control section 24 displays the calculation results in a display section to be seen by the user and/or stores the calculation results in a storage section to maintain a record. Of course, the calculation results may be transmitted to an external device via an interface.

Next, the control section 24 judges whether there are end instructions from the user (step S207). If it is determined that there are no end instructions from the user, the control section 24 returns to step S202 and continues the measurement control. On the other hand, if it is judged that there are end instructions from the user, this process flow is ended.

The first embodiment described above is useful for removing the effect of substances other than the gaseous body sample that adsorb to the trapping body 14 trapping the microparticles, for example, and the second embodiment described above is useful for removing the effect of noise components that change over time, for example. Furthermore, the first embodiment is preferable if the microparticles of the analysis target are volatile substances, and both the first embodiment and the second embodiment are suitable if the microparticles are refractory substances. Both the first embodiment and the second embodiment have the feature of introducing the sample gas and the comparative gas into the gas analyzer 20 repeatedly in an alternating manner, and attempt to increase the speed of the composition analysis by directly calculating the difference amount without accumulating intensity values output by the gas analyzer 20.

For example, when analyzing microparticles in exhaust gas that is expelled by a large-scale factory or the like, the concentration of microparticles is higher than the concentration of these microparticles in the atmosphere, and therefore there is no need to accumulate these microparticles for the measurement. On the other hand, when reflecting analysis results in factory control, a higher-speed analysis cycle is necessary. Accordingly, the microparticle composition analyzing apparatus according to the first embodiment or the second embodiment is suitable for use in such a system.

On the other hand, when measuring a harmful substance contained in the atmosphere within a residential environment, the concentration of microparticles in the measurement target is generally low, and it is necessary to accumulate these microparticles for the measurement. In this case, the analysis cycle usually does not need to be especially fast. Therefore, a third embodiment is described below that is suitable for such conditions.

The third embodiment has the same apparatus structure as the microparticle composition analyzing apparatus 100 of the first embodiment. However, the control and calculation method are different than in the first embodiment. Specifically, the time span B for the sample air described in FIG. 3 is set to be a longer time according to the concentration of the microparticles that are the analysis target, and an amount of these microparticles needed for the analysis is accumulated by the trapping body 14. According to this setting, the time span A for the processed air is also set to a longer time. The control section 24 causes the accumulated microparticles to be pulse-irradiated with the laser 16*a* to generate the sample gas, and introduces this sample gas into the gas analyzer 20. The pulse irradiation may be a single instance of irradiation or multiple instances of irradiation. In the same manner, the comparative gas is generated from the processed air and introduced into the gas analyzer 20. The gas analyzer 20 performs the calculation schematically shown in FIGS. 10A to 10C.

Figure 10:
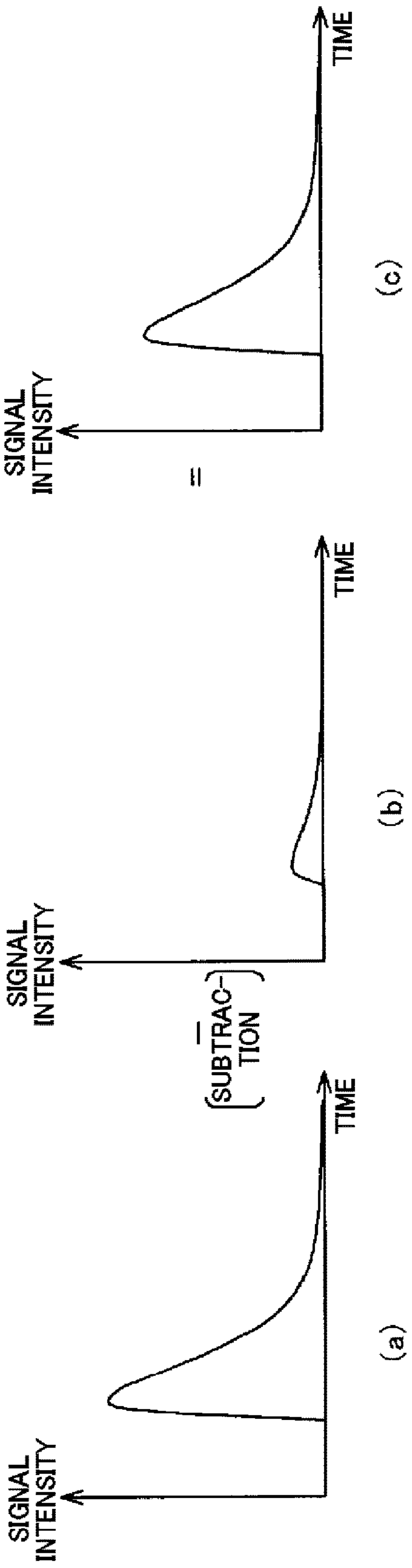
FIG. 10 is a drawing for describing the calculation process of the calculating section in the third embodiment.

FIG. 10 is a drawing for describing the calculation process of the calculating section 25 in the third embodiment. In each of the graphs (a) to (c) in FIG. 10, the horizontal axis indicates time and the vertical axis indicates the signal intensity output from the gas analyzer 20.

The graph (a) in FIG. 10 shows change over time of the signal intensity of the gas analyzer 20 for the sample gas. It is seen that immediately after the sample gas is introduced, the signal intensity increases sharply and then gradually decreases. The graph (b) in FIG. 10 shows change over time of the signal intensity of the gas analyzer 20 for the comparative gas. It is seen that immediately after the comparative gas is introduced, the signal intensity increases slightly and then decreases gently within a short time. The graph (c) in FIG. 10 is a graph obtained by subtracting the change over time of the signal intensity shown in the graph (b) in FIG. 10 from the change over time of the signal intensity shown in the graph (a) in FIG. 10. The change over time shown in the graph (c) in FIG. 10 can be said to be the change of the signal intensity caused by the specified component of the microparticles contained in the sample air. When this graph is integrated, it is possible to calculate the amount of target microparticles within the acquired sample air.

The first to third embodiments are described above, but the microparticle composition analyzing apparatus 200 of the second embodiment has a structure that is substantially contained within the apparatus structures of the microparticle composition analyzing apparatus 100 of the first embodiment and the microparticle composition analyzing apparatus 100 of the third embodiment. Accordingly, the structure of the microparticle composition analyzing apparatus 100 can be used as-is to perform the control described as the second embodiment. In other words, if the structure of the microparticle composition analyzing apparatus 100 is used, it is possible to selectively switch between the types of control according to the microparticles that are the analysis target. Specifically, the control section 24 need only determine whether to use gas generated by radiating the laser 16*a* into the processed air obtained by performing the cleaning process on the comparative gas or use gas existing near the irradiation location of the laser 16*a* during a time period when the laser 16*a* is not irradiating the microparticles.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

LIST OF REFERENCE NUMERALS

10: aerodynamic lens, 10*a*: particle stream, 10*b*: inlet, 10*c*: outlet, 12: skimmer, 12*a*: through-hole, 14: trapping body, 16: laser apparatus, 16*a*: laser, 18: analysis cell, 18*a*: skimmer portion, 18*b*: through-hole, 18*c*: small hole, 20: gas analyzer, 20*a*: ionization region, 22: processed air supplying section, 24: control section, 25: calculating section, 26: reduced pressure chamber, 26*a*: first reduced pressure chamber, 26*b*: second reduced pressure chamber, 26*c*: third reduced pressure chamber, 27*a*: first exhaust apparatus, 27*b*: second exhaust apparatus, 27*c*: third exhaust apparatus, 28: first dividing wall, 29: second dividing wall, 30: inlet pipe, 30*a*: first path, 30*b*: second path, 30*c*: third path, 32: optical window, 33: optical window, 100: microparticle composition analyzing apparatus, 200: microparticle composition analyzing apparatus.

What is claimed is:

1. A microparticle composition analyzing apparatus that analyzes composition of microparticles contained in a gaseous sample by oxidizing the microparticles to release a sample gas and analyzing the sample gas and a comparative gas, which is the gaseous sample apart from the microparticles, comprising:

a chamber having an entrance and an exhaust;

an exhaust apparatus coupled to the exhaust of the chamber, the exhaust apparatus configured to create a gas flow through the chamber from the entrance to the exhaust by reducing a pressure within the chamber;

an inlet pipe coupled to the entrance outside of the chamber, the inlet pipe including a first path and a second path, the second path including a filter, the first and second path converging into a single path, the entrance coupled to the single path;

a control section configured to control the gas flow through the first path and the second path;

a trapping section within the chamber, the trapping section configured to trap microparticles in the gas flow;

a laser apparatus configured to radiate laser light toward the trapping section, the laser light operable to oxidize and release the sample gas from trapped microparticles; and a gas analyzer within the chamber downstream of the trapping section, the gas analyzer configured to analyze gaseous components of the sample gas and the comparative gas, wherein the control section is further configured to control a time span for introducing the gas flow from the first path, which causes analysis of the sample gas, and the second path, which causes analysis of the comparative gas to be separated from each other by a dead time span, during which the gas flow is prevented.

2. The microparticle composition analyzing apparatus according to claim 1, further comprising:

a calculating section configured to calculate a difference amount between a first signal intensity and a second signal intensity that correspond to a specified component contained in the gaseous sample, the first signal intensity obtained from the gas analyzer upon introduction of the gas flow through the first path and the second signal intensity obtained from the gas analyzer upon introduction of the gas flow through the second path.

3. The microparticle composition analyzing apparatus according to claim 1, wherein upon introduction of the gas flow through the second path, a gas generated by irradiating, with the laser light, the gas flow having the microparticles filtered by the filter is introduced into the gas analyzer as the comparative gas.

4. The microparticle composition analyzing apparatus according to claim 1, wherein the filter included in the second path is configured to remove the microparticles from the gaseous sample.

5. The microparticle composition analyzing apparatus according to claim 1, wherein the control section sequentially switches between the gas flow through the first path and the gas flow through the second path and supplies the corresponding gas flow to the trapping section irradiated by the laser light.

6. The microparticle composition analyzing apparatus according to claim 1, wherein upon sequential introduction of the gas flow through the first path and the second path, the sample gas generated by pulse-irradiating the microparticles contained in the gaseous sample with the laser light and the comparative gas generated by pulse-irradiating, with the laser light, the gas flow having the microparticles filtered by the filter are sequentially introduced into the gas analyzer.

7. The microparticle composition analyzing apparatus according to claim 1, wherein upon repeated introduction of the gas flow through the first path and the second path in an alternating manner, the sample gas generated by continuously irradiating the microparticles contained in the gaseous sample with the laser light and the comparative gas generated by continuously irradiating, with the laser light, the gas flow having the microparticles filtered by the filter are repeatedly introduced into the gas analyzer in the alternating manner.

8. The microparticle composition analyzing apparatus according to claim 7, wherein the control section controls the gas flow through the first path and the second path, such that the sample gas and the comparative gas are introduced into the gas analyzer in an alternating manner with a predetermined period.

9. The microparticle composition analyzing apparatus according to claim 7, wherein the control section controls the gas flow through the first path and the second path, such that the sample gas and the comparative gas are introduced into the gas analyzer in an alternating manner with a timing adjusted based on a signal intensity corresponding to the gaseous components introduced into the gas analyzer.

10. The microparticle composition analyzing apparatus according to claim 1, wherein the control section suspends radiation of the laser light during a time period corresponding to the dead time span.

11. A microparticle composition analyzing apparatus that analyzes composition of microparticles contained in a gaseous sample by oxidizing the microparticles to release a sample gas and analyzing the sample gas and a comparative gas, which is the gaseous sample apart from the microparticles, comprising:

a chamber having an entrance and an exhaust;

an exhaust apparatus coupled to the exhaust of the chamber, the exhaust apparatus configured to create a gas flow through the chamber from the entrance to the exhaust by reducing a pressure within the chamber;

an inlet pipe coupled to the entrance outside of the chamber;

a trapping section within the chamber, the trapping section configured to trap microparticles in the gas flow;

a laser apparatus configured to radiate laser light toward the trapping section, the laser light operable to oxidize and release the sample gas from trapped microparticles;

a gas analyzer within the chamber downstream of the trapping section, the gas analyzer configured to analyze gaseous components of the sample gas and the comparative gas; and a control section configured to control a timing of a radiation of the laser light, such that the gas flow that is irradiated with the laser light, which causes analysis of the sample gas, and the gas flow that is not irradiated with the laser light, which causes analysis of the comparative gas, are sequentially introduced into the gas analyzer.

12. The microparticle composition analyzing apparatus according to claim 11, wherein the control section controls the timing of the radiation of the laser light, such that the sample gas generated by irradiating the microparticles contained in the gas flow with the laser light and the gas flow that is present near the trapping section while the laser light is not radiated are repeatedly introduced into the gas analyzer in an alternating manner.

13. The microparticle composition analyzing apparatus according to claim 12, wherein the control section controls the timing of the radiation of the laser light, such that the laser apparatus radiates the laser light with a predetermined period.

14. The microparticle composition analyzing apparatus according to claim 12, wherein the control section controls the timing of the radiation of the laser light by adjusting the timing based on a signal intensity corresponding to the gaseous components introduced into the gas analyzer.

15. A microparticle composition analyzing apparatus that analyzes composition of microparticles contained in a gaseous sample by oxidizing the microparticles to release a sample gas and analyzing the sample gas and a comparative gas, which is the gaseous sample apart from the microparticles, comprising:

a chamber having an entrance and an exhaust;

an exhaust apparatus coupled to the exhaust of the chamber, the exhaust apparatus configured to create a gas flow through the chamber from the entrance to the exhaust by reducing a pressure within the chamber;

an inlet pipe coupled to the entrance outside of the chamber, the inlet pipe including a first path and a second path, the second path including a filter, the first and second path converging into a single path, the entrance coupled to the single path;

a trapping section within the chamber, the trapping section configured to trap microparticles in the gas flow;

a laser apparatus configured to radiate laser light toward the trapping section, the laser light operable to oxidize and release the sample gas from trapped microparticles;

a gas analyzer within the chamber downstream of the trapping section, the gas analyzer configured to analyze gaseous components of the sample gas and the comparative gas, wherein; and a control section configured to (i) control the gas flow through the first path and the second path and control a time span for introducing the gas flow from the first path, which causes analysis of the sample gas, and the second path, which causes analysis of the comparative gas to be separated from each other by a dead time span, during which the gas flow is prevented, and (ii) control a timing of a radiation of the laser light such that the gas flow that is irradiated with the laser light, which causes analysis of the sample gas, and the gas flow that is not irradiated with the laser light, which causes analysis of the comparative gas, are sequentially introduced into the gas analyzer, wherein the control section is further configured to determine whether gas generated by irradiating, with the laser light, the gas flow through the second path or the gas flow, through the first path, that is present near the trapping section while the laser light is not radiated is introduced into the gas analyzer, sequentially with gas generated by irradiating, with the laser light, the microparticles contained in the gas flow through the first path.

* * * * *